United States Patent
Storm (10) Patent No.: US 8,239,016 B2
(45) Date of Patent: Aug. 7, 2012

(54) DETECTION OF PAIN/AWAKENING INTEGRAL VALUE

(75) Inventor: Hanne Storm, Oslo (NO)

(73) Assignee: Med Storm Innovation AS, Oslo (NO)

( * ) Notice: Subject to any disclaimer, the term of this patent is extended or adjusted under 35 U.S.C. 154(b) by 535 days.

(21) Appl. No.: 12/513,853

(22) PCT Filed: Nov. 8, 2007

(86) PCT No.: PCT/NO2007/000394
§ 371 (c)(1),
(2), (4) Date: Jun. 17, 2009

(87) PCT Pub. No.: WO2008/056991
PCT Pub. Date: May 15, 2008

(65) Prior Publication Data
US 2010/0056943 A1 Mar. 4, 2010

(30) Foreign Application Priority Data

Nov. 10, 2006 (NO) .................................... 20065167

(51) Int. Cl.
*A61B 5/05* (2006.01)
*A61B 19/00* (2006.01)
(52) U.S. Cl. ........ 600/547; 600/300; 600/306; 600/554; 600/557
(58) Field of Classification Search .................. 600/300, 600/306, 544, 554, 557, 547
See application file for complete search history.

(56) References Cited

U.S. PATENT DOCUMENTS 5,906,208 A 5/1999 Ishikawa et al.

FOREIGN PATENT DOCUMENTS

| EP | 1563789 | 8/2005 |
|---|---|---|
| JP | 08112253 | 5/1994 |
| WO | WO 00/72751 | 10/2000 |
| WO | WO 03/077748 | 9/2003 |
| WO | WO 03/094726 A1 | 11/2003 |

OTHER PUBLICATIONS

H. Storm et al.: "Skin conductance correlates with perioperative stress", Acta Anaesthesiologica Scandinavica, vol. 46, No. 7, Aug. 2002, pp. 887-895, XP008045947.

H. Storm et al.: "The development of a software program for analyzing spontaneous and externally elicited skin conductance changes in enfants and adults", Clinical Neurophysiology, Elsevier Science, IE, vol. 111, No. 10, Oct. 2000, pp. 1889-1898, XP002436196.

T. Ledowski et al: "New parameters of skin conductance compared with bispectral index ((R)) monitoring to assess emergence from total intravenous anaesthesia", British Journal of Anaesthesia, BJM Publishing Group, London, GB, vol. 99, No. 4, 2007, pp. 547-551, XP009096174.

*Primary Examiner* — Jeffrey G Hoekstra
*Assistant Examiner* — Megan Leedy
(74) *Attorney, Agent, or Firm* — Christian D. Abel (57) ABSTRACT

The invention relates to a method and an apparatus for monitoring the autonomous nervous system of a sedated patient. A skin conductance signal is measured at an area of the patient's skin during a measurement interval. A first measure and a second measure, both reflecting the state of the autonomous nervous system of the patient, is calculated by means of certain integral functions. The largest one of the first and second measures is then selected as the output signal (Y) that reflects the state of the autonomous nervous system of the sedated patient.

12 Claims, 4 Drawing Sheets

DETECTION OF PAIN/AWAKENING INTEGRAL VALUE

TECHNICAL FIELD

The invention relates in general to medical technology, and in particular to a method and an apparatus for monitoring a sedated patient.

BACKGROUND OF THE INVENTION

During surgery it is very important to observe the patient's level of consciousness and awareness. Few reliable methods of observation exist today. In the field of medical technology there is a problem in producing physical measurements representing the activity in an individual's autonomous nervous system, i.e. in the part of the nervous system, which is beyond the control of the will.

Particularly, there is a special need to monitor the autonomous nervous system of a sedated, non-verbal patient, e.g. a patient in anaesthesia or an artificially ventilated patient, in order to detect if the patient needs more hypnotics because of awakening stimuli or more analgesia because of pain stimuli.

Tests have shown that the skin's conductance changes as a time variable signal which, in addition to a basal, slowly varying value (the so-called basal level or the average conductance level through a certain interval), also has a component consisting of spontaneous waves or fluctuations.

The basal level and the characteristics of the fluctuations may be viewed on a display by a skilled, human operator (e.g., the surgeon or the anesthesiologist), in order to monitor the autonomous nervous system of the patient.

However, in order to improve comprehensibility, as well as convenience and ease of operation, there is still a need to provide a method and an apparatus that will present one single measure which reflects the autonomous nervous system state.

RELATED BACKGROUND ART

WO-03/94726 discloses a method and an apparatus for monitoring the autonomous nervous system of a sedated patient. In the method, a skin conductance signal is measured at an area of the patient's skin. Certain characteristics, including the average value of the skin conductance signal through a time interval and the number of fluctuation peaks through the interval, is calculated. Based on these characteristics, two output signals are established, indicating pain discomfort and awakening in the patient, respectively. The awakening signal is established based on the number of fluctuations and the average value through an interval.

SUMMARY OF THE INVENTION

An object of the present invention is to provide a method and an apparatus for monitoring a sedated patient.

Another object of the invention is to provide such a method and apparatus, which relies on the measurement of skin conductance variations due to emotional sweating.

Still another object of the invention is to provide such a method and apparatus, which provides reliable output indications.

A further object of the invention is to provide such a method and apparatus which overcomes disadvantages of the related prior art.

Still another object of the invention is to provide such a method and apparatus, which substantially differ from the related prior art.

According to the invention, at least one of the above objects are achieved by a method and an apparatus as defined in the appended claims Further advantages and characteristics of the invention are indicated in the dependent claims.

BRIEF DESCRIPTION OF THE DRAWINGS

The principle of the invention will be disclosed in the following by an example embodiment, illustrated in the figures.

DETAILED DESCRIPTION OF THE INVENTION

Figure 1:
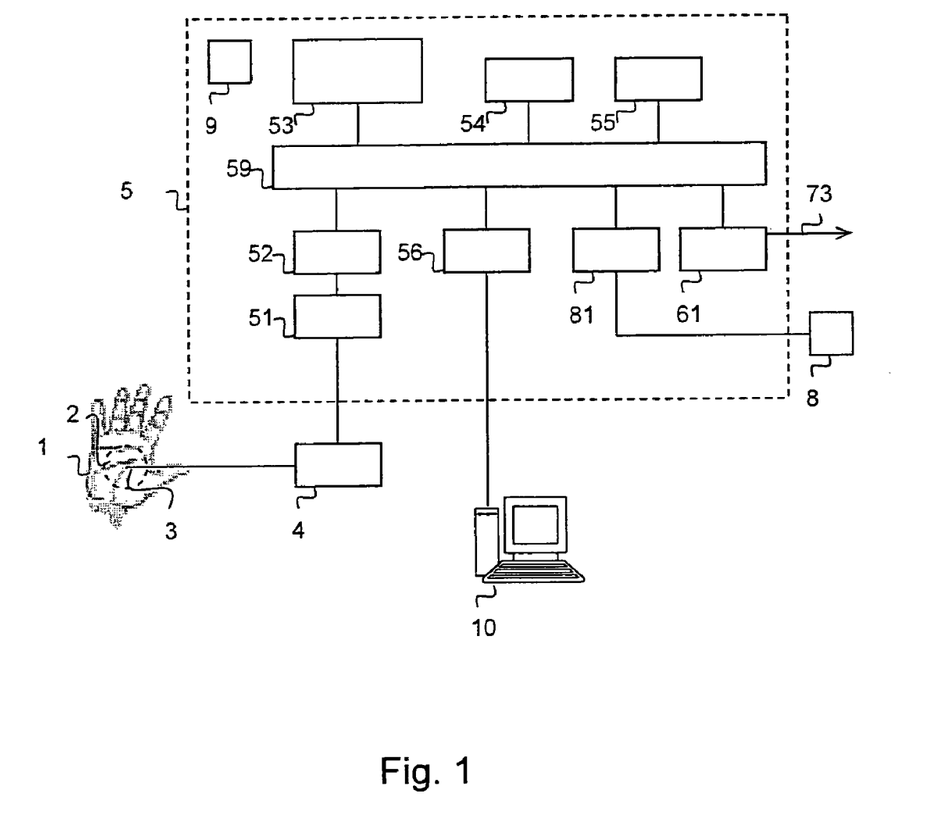
FIG. 1 illustrates a block diagram for a preferred embodiment of an apparatus according to the invention.

FIG. 1 illustrates a block diagram for a preferred embodiment of an apparatus according to the invention.

Substantial parts of the apparatus' hardware structure is previously described in the Applicant's related patent application published as WP-03/94726, with particular reference to the block diagram in the publication's FIG. 1 and the corresponding, detailed description. The disclosure of this publication, and the apparatus hardware structure in particular, is hereby expressly incorporated by reference.

On an area 2 of the skin on a body part 1 of the patient, sensor means 3 are placed for measuring the skin's conductance. The body part 1 is preferably a hand or a foot, and the area 2 of the skin on the body part 1 is preferably the palmar side of the hand or the plantar side of the foot. Alternatively, the body part 1 may be the forehead of the patient. The sensor means 3 comprise contact electrodes where at least two electrodes are placed on the skin area 2. In a preferred embodiment the sensor means 3 consist of three electrodes: a signal electrode, a measuring electrode and a reference voltage electrode, which ensures a constant application of voltage over the stratum corneum (the surface layer of the skin) under the measuring electrode. The measuring electrode and the signal electrode are preferably placed on the skin area 2. The reference voltage electrode may also be placed on the skin area 2, but it is preferably placed in a nearby location, suitable for the measuring arrangement concerned.

In an embodiment, an alternating current is used for measuring the skin's conductance. The alternating current advantageously has a frequency in the range of up to 1000 Hz, such as 88 Hz. A signal generator, operating at the specified frequency, applies a signal current to the signal electrode.

The resulting current through the measuring electrode is conveyed to a measurement converter 4, which includes a current to voltage converter and a decomposition circuit which provides the conductance real part of the complex admittance.

The measurement converter 4 may also comprise amplifier and filter circuits. In the preferred embodiment the measurement converter contains low-pass filters, both at the input and at the output. The object of the input low-pass filter is to attenuate high-frequency noise, for instance coming from other medical equipments, and also to serve as anti-aliasing filter to prevent high frequency components from being received by subsequent circuits for time discretization.

The control unit 5 comprises a time discretization unit 51 for time discretization of the signal from the measurement converter. The time discretization takes place at a sampling rate, which may advantageously be in the order of 20 to 200 samplings per second. The control unit further comprises an analog-digital converter 52, which converts measurement data to digital form.

The control unit 5 also comprises a processing unit 53 for processing the digitized measurement data, storage means in the form of at least one store for storing data and programs, illustrated as a non-volatile memory 54 and a random access memory 55. The control unit 5 further comprises an output interface circuit 61, which provides an output signal 73. Preferably, the control unit 5 further comprises a display interface circuit 81, which is further connected to display unit 8. The control unit 5 may also advantageously comprise a communication port 56 for digital communication with an external unit, such as a personal computer 10.

In a preferred embodiment the non-volatile memory 54 comprises a read-only storage in the form of programmable ROM circuits, or alternatively Flash memory circuits, containing at least a program code and permanent data, and the random access memory 55 comprises RAM circuits, for storage of measurement data and other provisional data.

The control unit 5 also comprises an oscillator (not shown), which delivers a clock signal for controlling the processing unit 53. The processing unit 53 also contains timing means (not shown) in order to provide an expression of the current time, for use in the analysis of the measurements. Such timing means are well-known to those skilled in the art, and are often included in micro controllers or processor systems which the skilled person will find suitable for use with the present invention.

The control unit 5 may be realized as a microprocessor-based unit with connected input, output, memory and other peripheral circuits, or it may be realized as a micro controller unit where some or all of the connected circuits are integrated. The time discretization unit 51 and/or analog-digital converter 52 may also be included in such a unit. The choice of a suitable form of control unit 5 involves decisions, which are suitable for a person skilled in the art.

An alternative solution is to realize the control unit as a digital signal processor (DSP).

According to the invention, a novel and inventive method is performed by the control unit 5, in order to analyze the skin conductance signal. By means of the program code, the control unit 5 is particularly arranged to perform the method in accordance with the invention, such as the method exemplified with reference to FIG. 2 below.

The control unit 5 is arranged to read time-discrete and quantized measurements for the skin conductance from the measurement converter 4, preferably by means of an executable program code, which is stored in the non-volatile memory 54 and which is executed by the processing unit 53. It is further arranged to enable measurements to be stored in the read and write memory 55. By means of the program code, the control unit 5 is further arranged to analyze the measurements in real time, i.e. simultaneously or parallel with the performance of the measurements.

In this context, simultaneously or parallel should be understood to mean simultaneously or parallel for practical purposes, viewed in connection with the time constants which are in the nature of the measurements. This means that input, storage and analysis can be undertaken in separate time intervals, but in this case these time intervals, and the time between them, are so short that the individual actions appear to occur concurrently.

The control unit 5 is further arranged to identify the fluctuations in the skin conductance signal. In particular, the control unit 5 is arranged to identify minimum points in the skin conductance signal.

The control unit 5 is further arranged to select a first local minimum point of the skin conductance signal as a first local minimum point in the measurement interval. The control unit 5 is also arranged to search for a last local minimum point of the skin conductance signal as a last local minimum point in the measurement interval.

The control unit 5 is further arranged to calculate a linear ramp function defined by certain points on the skin conductance curve, in particular between two subsequent minimum points.

The control unit 5 is further arranged to compare the skin conductance value with the corresponding linear ramp function at any point in a measurement interval.

The control unit 5 is further arranged to calculate an approximation of the integral of a function with respect to time, through an integrating interval.

Further functions of the control unit are described below with reference to the method illustrated in FIG. 2.

All the above mentioned functions of the control unit 5 are achieved by appropriate computer program portions included in the memory, preferably the non-volatile memory 54.

The processing unit 53, the memories 54, 55, the analog/digital converter 52, the communication port 56, the interface circuit 81 and the interface circuit 61 are all connected to a bus unit 59. The detailed construction of such bus architecture for the design of a microprocessor-based instrument is regarded as well-known for a person skilled in the art.

The interface circuit 61 is a digital or analog output circuit, which generates a digital or analog representation of an output signal 73 from the processing unit 53 via the bus unit 59 when the interface circuit 61 is addressed by the program code executed by the processing unit 53.

The output signal 73 represents the calculated approximation of the integral of the skin conductance signal with respect to time, indicated above.

The output signal 73 reflects the state of the patient's autonomous nervous system as one single measure, which may be conveniently read and comprehended by a skilled, human operator, e.g., a surgeon or an anesthesiologist, in order to monitor the autonomous nervous system of the patient.

In a preferred embodiment the display 8 comprises a field or window for displaying the value of the output signal 73, either as a digital number, or as a graphic representation, or both. The display 8 may also advantageously be used for graphic visualization of the conductance signal, such as a time varying graph, as well as for displaying the frequency and amplitude of the measured signal fluctuations.

The apparatus further comprises a power supply unit 9 for supplying operating power to the various parts of the apparatus. The power supply may be a battery or a mains supply.

The apparatus may advantageously be adapted to suit the requirements regarding hospital equipment, which ensures patient safety. Such safety requirements are relatively easy to fulfill if the apparatus is battery-operated. If, on the other hand, the apparatus is mains operated, the power supply shall meet special requirements, or requirements are made regarding a galvanic partition between parts of the apparatus (for example, battery operated), which are safe for the patient and parts of the apparatus, which are unsafe for the patient. If the apparatus has to be connected to external equipment, which is mains operated and unsafe for the patient, the connection between the apparatus, which is safe for the patient and the unsafe external equipment requires to be galvanically separated. Galvanic separation of this kind can advantageously be achieved by means of an optical partition. Safety requirements for equipment close to the patient and solutions for fulfilling such requirements in an apparatus like that in the present invention are well-known to those skilled in the art FIG. 2 illustrates a flow chart of a method according to the invention.

The method is preferably executed by a processing device in an apparatus for providing an output signal that reflects the state of the autonomous nervous system of a sedated patient, e.g. the processing device 53 in the control unit 5 illustrated in FIG. 1.

The method starts at the initial step 200.

In the introductory step 202, a stimulus is exerted to the patient. Advantageously, this stimulus is a pain-inducing stimulus, in particular a standardised noxious stimulus. To this end, equipment specialized to activate the C-fibers may be used. More advantageously, equipment activating many nerves including C-fibers like a tetanic noxious stimuli may be used.

The step 202 may be performed manually by an operator. Alternatively, the step 202 may be performed by the control unit 5, in which case a pain stimulating device (not illustrated in the figures) is operatively connected to the control unit 5 and arranged for exerting a stimulus to the patient.

Alternatively, step 202 may be omitted, i.e. the method may also be used without exerting an external stimulus to the patient.

Next, in the signal providing step 210, a conductance signal $u(t)$ measured at an area of the patient's skin is provided through a measurement interval.

Next, in the identifying step 212, a local minimum point of the skin conductance signal are identified through the measurement interval.

Next, in the selecting step 214, the intervals between the identified, subsequent minimum points within the measurement interval are selected as integrating intervals for the further calculations.

Next, in the first measure calculating step 220, a first measure that reflects the state of the autonomous nervous system of the sedated patient is calculated.

The calculating of the first measure is based on a repeated acquiring and processing of the skin conductance signal $u(t)$ in the range T1 to T2, corresponding to an integrating interval.

For each integrating interval [T1, T2], a linear ramp function $v(t)$ is defined as the straight line extending from the first to the last point on the $u(t)$ curve in the integrating interval [T1, T2]. Thus, the line extends from the point (T1, u(T1)) to the point (T2, u(T2)). The linear ramp function follows the equation $$v(t) = u(T1) + \frac{u(T2) - u(T1)}{T2 - T1} t \tag{1}$$

The first measure is calculated as a sum of integrals through the measurement intervals.

The function to be integrated in each integrating interval is zero in subintervals wherein $u(t) \leq v(t)$, i.e. wherein the skin conductance curve is lower than or equal to the linear ramp.

The function to be integrated in each integrating interval is $(u(t)-v(t))dt$ in subintervals wherein $u(t) > v(t)$, i.e, wherein the skin conductance curve exceeds the linear ramp.

This implies that in subintervals wherein $u(t) \leq v(t)$, no contribution will be added to the integral. In subintervals wherein $u(t) > v(t)$, the area between the skin conductance curve and the linear ramp will be added as a contribution to the integral and thus to the first measure.

This integration calculation is performed for each integrating interval, and the sum of such intervals through the entire measurement interval is provided as the first measure that reflects the state of the autonomous nervous system of the sedated patient.

Thus, the first measure may be calculated in the calculating step 220 by the following formula:

$$\text{first\_measure} \approx \sum_{measurement\_interval} \int_{T1}^{T2} \begin{cases} 0 dt & \text{if } u(t) \leq v(t) \\ (u(t) - v(t))dt & \text{if } u(t) > v(t) \end{cases} \tag{2}$$

wherein $u(t)$ is the measured skin conductance signal, T1 and T2 are the starting point and ending point, respectively, of each integrating interval.

T1 and T2 are local minimum points of the skin conductance signal. In the summing process over the measurement interval, T1 and T2 will assume new, larger values for each added integration term.

In the present specification, the term "integral" should be interpreted as an approximation to the exact integral. Likewise, the term "integrating" should be interpreted as calculating an approximation to the exact integral. Advantageously, a numeric integration method such as a rectangle method, a trapezoidal method or a method based on Simpson's rule is employed in the calculating step 220.

The skilled person will realize that the calculation step 220 may include to precalculate any intersecting points between the skin conductance curve $u(t)$ and the linear ramp $v(t)$. It will also be realized that subintervals may be defined by means of such intersecting points and possibly the start point T1 or the end point T2. In such a sub-interval, if $u(t) \leq v(t)$ at some point in the sub-interval, the entire subinterval may be neglected in the integrating calculation, since it will be certain that the entire subinterval shall not contribute to the first measure.

Next, in the second calculating step 230, a second term that reflects the state of the autonomous nervous system of the sedated patient is calculated.

The second measure is calculated as an integral through the interval from T_first through T_last, wherein T_first is the first local minimum point in the measurement interval, T_last is selected from the group consisting of the last local minimum point in the measurement interval, or the last point in the measurement interval.

The function to be integrated in the interval [T_first to T_last] is zero in subintervals wherein $u(t) \leq u(T\_first)$, i.e. wherein the current skin conductance value is lower than or equal to the skin conductance value at the point T_first.

The function to be integrated in the interval [T_first to T_last] is $(u(t)-u(T\_first))dt$ in subintervals wherein $u(t) \geq u(T\_first)$, i.e. wherein the current skin conductance is greater than the skin conductance value at time T_first.

This implies that in subintervals where the current skin conductance value is lower than or equal to the skin conductance value at the point T_first, no contribution will be added to the second measure. On the other hand, in subintervals where the current skin conductance is greater than the skin conductance value at the point T_first, the difference between the skin conductance value and the skin conductance value at time T_first will be integrated with respect to time, and the result will contribute to the second measure.

More specifically, the second measure is calculated in step 230 as $$\text{second\_measure} \approx \int_{T\_first}^{T\_last} \begin{cases} 0 dt & \text{if } u(t) \leq u(T\_first) \\ (u(t) - u(T\_first))dt & \text{if } u(t) > u(T-first) \end{cases} \quad (3)$$

wherein u(t) is the measured skin conductance signal, T_first is the first local minimum point in the measurement interval, T_last is the last point in the measurement interval or the last local minimum point in the measurement interval.

The skilled person will realize that the calculation step 230 may include to precalculate any intersecting points between the skin conductance curve u(t) and the straight line represented by the constant value u(T_first). It will also be realized that subintervals may be defined by means of such intersecting points and possibly the start point T_first or the end point T_last. In such a sub-interval, if u(t)≦u(T_first) at some point in the sub-interval, the entire subinterval may be neglected in the integrating calculation, since it will be certain that the entire subinterval shall not contribute to the second measure.

In the first comparison step 240, the calculated first and second measures are compared. If the first measure is the largest, the first measure is provided in step 242 as the output signal Y that reflects the state of the autonomous nervous system of a sedated patient. On the contrary, if the first measure is not the largest, the second measure is provided in step 244 as the output signal Y that reflects the state of the autonomous nervous system of a sedated patient. In effect, the largest one of the first and second measures is provided as the output signal Y.

The output signal Y is advantageously displayed (not illustrated as a separate step in FIG. 2) on the display 8.

The output signal, e.g. viewed on a display on the apparatus that executes the method according to the invention, reflects the state of the patient's autonomous nervous system as one single measure. The invention provides a high degree of comprehensibility, convenience and ease of operation when the apparatus is operated by a skilled, human operator (e.g., a surgeon or anesthesiologist).

The method may be further improved by including the second comparison step 250, wherein it is determined if the output signal Y is within a predetermined range <Y1, Y2> of output signal values.

Advantageously, Y1 is in the range <0.05 μSs, 0.20 μSs>. More preferably, Y1 is in the range <0.08 μSs, 0.12 μSs>. Most preferably, Y1 is about 0.1 μSs.

Advantageously, Y2 is in the range <0.5 μSs, 3.0 μSs>. More preferably, Y2 is in the range <0.8 μSs, 2.2 μSs>. Most preferably, Y2 is about 2.0 μSs.

If the second comparison is true, a pain indication signal is set in step 262, and the process is advantageously repeated from the skin conductance providing step 210. Otherwise, the process continues, advantageously at the third comparison step 260 below.

The method may also be further improved by including the third comparison step 270, wherein it is determined if the output signal Y is larger than a predetermined output signal value Y3.

Advantageously, Y3 is in the range <0.5 μSs, 3.0 μSs>. More preferably, Y3 is in the range <0.8 μSs, 2.2 μSs>. Most preferably, Y3 is about 2.0 μSs.

If this third comparison is true, an awakening indication signal is set in step 272, and the process is advantageously repeated from step the skin conductance providing step 210. Otherwise, the process continues, advantageously at the terminating test step 270 below.

The overall process is advantageously reiterated or repeated. In order to terminate the process, a terminating test step 270 is advantageously provided, wherein a test is performed in order to determine if the process should be terminated. If so, the process terminates at step 290. Otherwise, the process is repeated from the skin conductance providing step 210.

Figure 3:
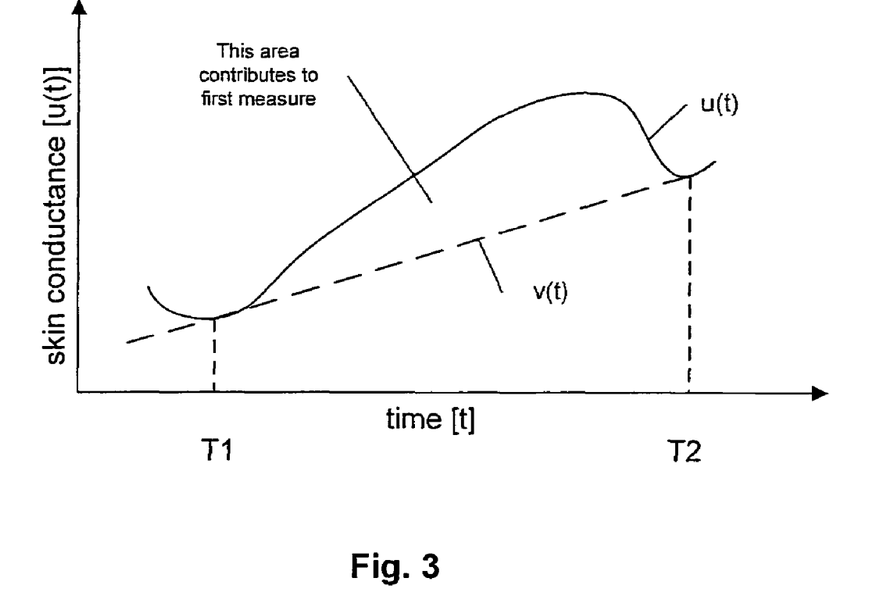
FIG. 3 shows a sample skin conductance measurement graph, in order to illustrate the calculation of a first measure in the method according to the invention.

FIG. 3 shows a sample skin conductance measurement graphs, in order to illustrate the calculation performed in the calculating step 220, i.e. the calculating of a first measure in the method according to the invention.

The graph in FIG. 3 shows a section of a first skin conductance signal measured on a patient through a measurement interval. The duration of the measurement interval may be e.g. 15 sec. Within this measurement interval, local minimum points in the skin conductance signal have been identified, and the intervals between subsequent minimum points have been selected as integrating intervals.

One such integrating interval is illustrated in FIG. 3, starting at the local minimum point at T1 and the subsequent local minimum point at T2.

In the integrating interval [T1, T2] a linear ramp function v(t) is defined as the straight line extending from the first to the last point on the u(t) curve in the integrating interval [T1, T2]. Thus, the line extends from the point (T1, u(T1)) to the point (T2, u(T2)), as explained above with reference to FIG. 2.

In this example, u(t)>v(t) in the entire integrating interval [T1, T2]. Thus, in accordance with the explanation above with reference to FIG. 2, the first measure is calculated as the area between the u(t) curve and the v(t) curve, i.e. the integral from T1 through T2 of the difference (u(t)−v(t))dt.

This integration calculation is performed for each integrating interval, and the sum of such intervals through the entire measurement interval is provided as the first measure that reflects the state of the autonomous nervous system of the sedated patient.

Figure 4:
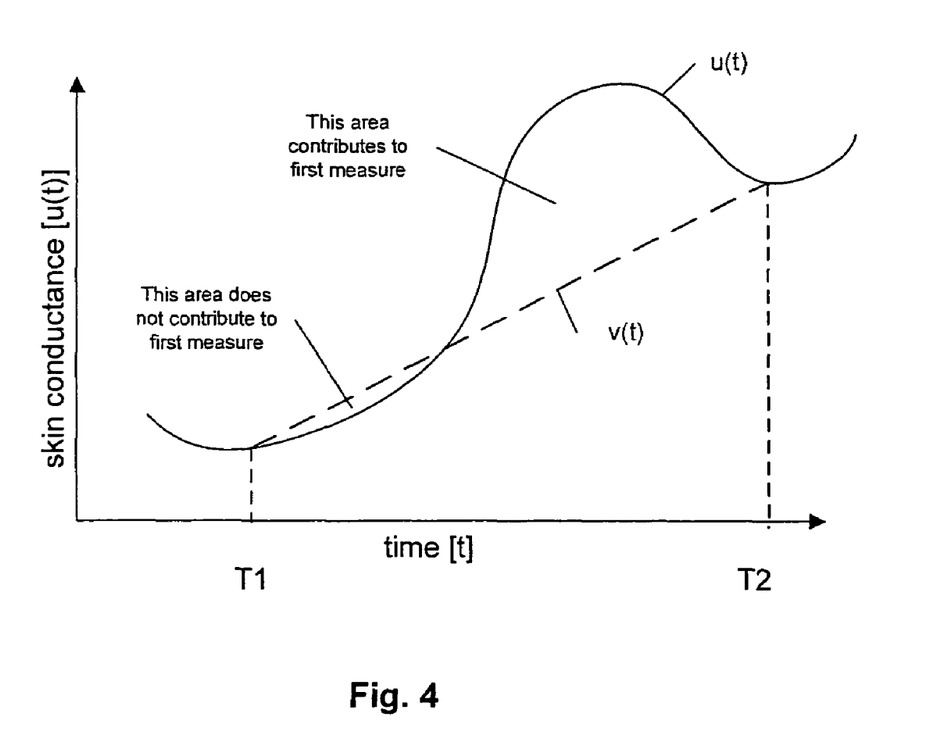
FIG. 4 shows a sample skin conductance measurement graph, in order to illustrate the calculation of a first measure in the method according to the invention.

FIG. 4 shows another sample skin conductance measurement graphs, also in order to illustrate the calculation performed in the calculating step 220, i.e. the calculating of a first measure in the method according to the invention.

The graph in FIG. 4 shows a section of a first skin conductance signal measured on a patient through a measurement interval. The duration of the measurement interval may be e.g. 15 sec. Within this measurement interval, local minimum points in the skin conductance signal have been identified, and the intervals between subsequent minimum points have been selected as integrating intervals.

One such integrating interval is illustrated in FIG. 4, starting at the local minimum point at T1 and the subsequent local minimum point at T2.

In the integrating interval [T1, T2] a linear ramp function v(t) is defined as the straight line extending from the first to the last point on the u(t) curve in the integrating interval [T1, T2]. Thus, the line extends from the point (T1, u(T1)) to the point (T2, u(T2)), as explained above with reference to FIG. 2.

In this example, $u(t) \leq v(t)$ in the first portion of the interval [T1, T2], i.e. the skin conductance curve is lower than or equal to the linear ramp. As explained above with reference to FIG. 2, the function to be integrated is zero in this interval portion. Thus, the area to the left in FIG. 4 does not contribute to the first measure.

As further illustrated in FIG. 4, in the second portion of the integrating interval [T1, T2], the skin conductance curve is greater than the linear ramp, i.e. $u(t) > v(t)$. In this portion of the integrating interval, the area between the u(t) curve and the v(t) curve, i.e. the integral from T1 through T2 of the difference $(u(t)-v(t))dt$, will contribute to the first measure.

This integration calculation is performed for each integrating interval, and the sum of such intervals through the entire measurement interval is provided as the first measure that reflects the state of the autonomous nervous system of the sedated patient.

Figure 5:
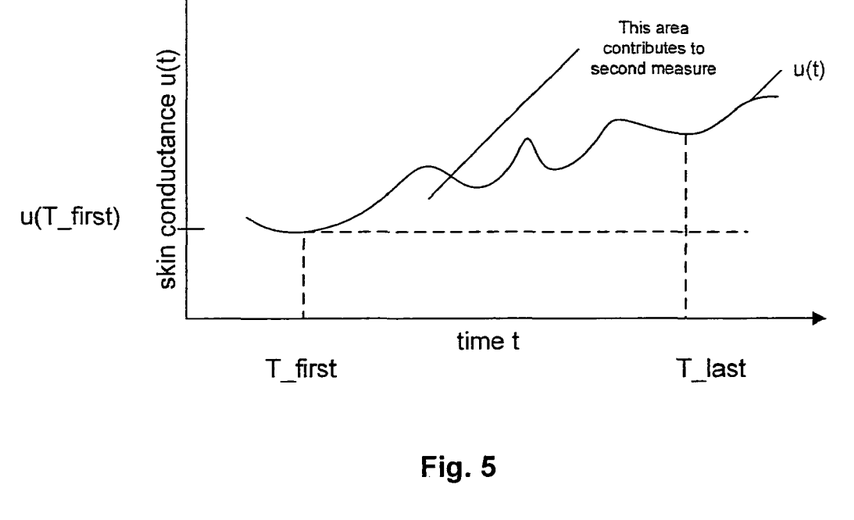
FIG. 5 shows a sample skin conductance measurement graph, in order to illustrate the calculation of a second measure in the method according to the invention.

FIG. 5 shows a sample skin conductance measurement graphs, in order to illustrate the calculation performed in the calculating step 230, i.e. the calculating of a second measure in the method according to the invention.

The graph in FIG. 5 shows a subset of a first skin conductance signal measured on a patient through a measurement interval. The duration of the measurement interval may be e.g. 15 sec. Within this measurement interval, the first local minimum point in the skin conductance signal has been identified and denoted T_first. This point is selected as the first point of the interval subset [T_first, T_last].

The last point in the interval subset [T_first, T_last] may either be the last point in the measurement interval or the last minimum point in the measurement interval. In the illustrated example in FIG. 5, the last minimum point is selected as T_last.

As appears from FIG. 5, $u(t) > u(T\_first)$ through the entire interval subset [T_first, T_last]. In accordance with the description above with reference to the calculating step 230 illustrated in FIG. 2, this implies that the second measure shall be calculated as the integral from T_first to T_last of the difference $(u(t)-u(T\_first))$ with respect to time. In other words, the second measure is calculated as the area between the u(t) curve and the horizontal line defined by the constant value u(T_first).

Figure 6:
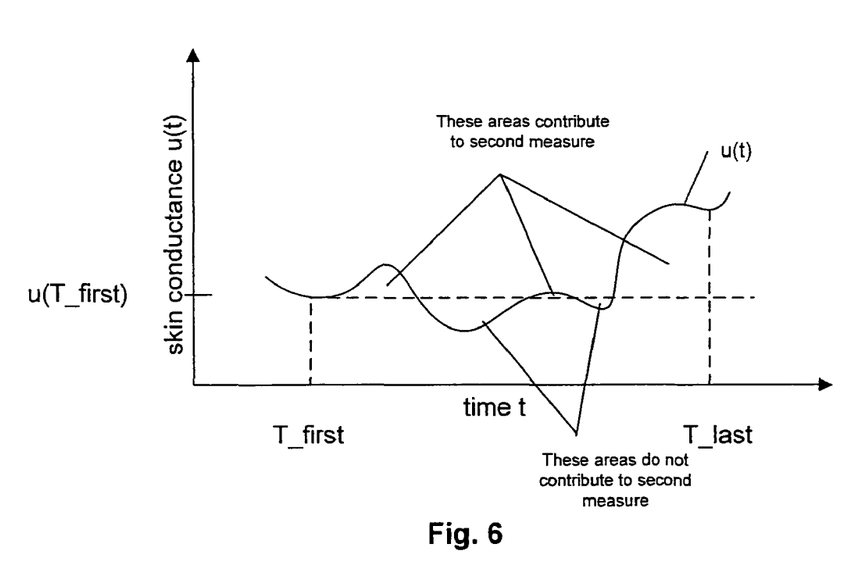
FIG. 6 shows a sample skin conductance measurement graph, in order to illustrate the calculation of a second measure in the method according to the invention.

FIG. 6 shows another sample skin conductance measurement graphs, also in order to illustrate the calculation performed in the calculating step 230, i.e. the calculating of a second measure in the method according to the invention.

The graph in FIG. 6 shows a subset of a first skin conductance signal measured on a patient through a measurement interval. The duration of the measurement interval may be e.g. 15 sec. Within this measurement interval, the first local minimum point in the skin conductance signal has been identified and denoted T_first. This point is selected as the first point of the interval subset [T_first, T_last].

The last point in the interval subset [T_first, T_last] may either be the last point in the measurement interval or the last minimum point in the measurement interval. In the illustrated example in FIG. 5, the last minimum point is selected as T_last.

As appears from FIG. 6, $u(t) > u(T\_first)$ in some portions of the interval subset [T_first, T_last] (above the horizontal dotted line), while $u(t) \leq u(T\_first)$ in other portions of the interval subset [T_first, T_last] (below the horizontal dotted line).

Figure 2:
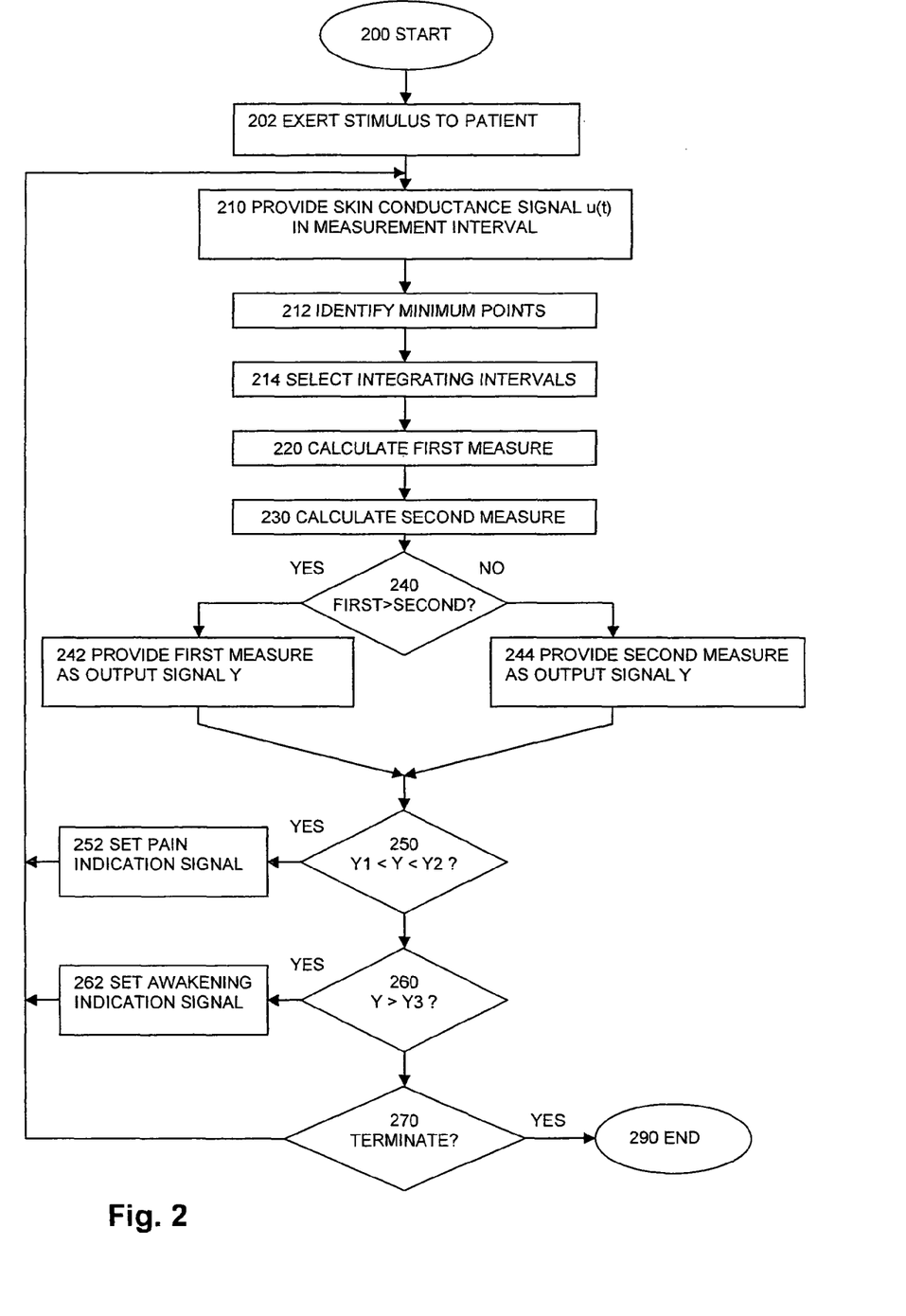
FIG. 2 illustrates a flow chart for a method according to the invention.

In accordance with the description above with reference to the calculating step 230 illustrated in FIG. 2, the second measure shall be calculated as the integral from T_first to T_last of the difference $(u(t)-u(T\_first))dt$ in the subintervals wherein $u(t) > u(T\_first)$. In the subintervals wherein $u(t) \leq u(T\_first)$, no contribution (zero) shall be added to the second measure.

In other words, the second measure is calculated as the sum of areas between the u(t) curve and the horizontal line defined by the constant value u(T_first), in the subintervals wherein $u(t) > u(T\_first)$.

The skilled person will realize that the output signal Y provided by the invention will be reduced in a phase during induction of anesthesia.

The above description and drawings present a specific embodiment of the invention. It will be obvious to the skilled person that alternative or equivalent embodiments exist within the scope of the present invention. For instance, the use of skin impedance instead of skin conductance will of course lead to equivalent results, if the inverse nature of these variables is taken into account.

When the term "patient" is used throughout the specification and claims, is should be appreciated that although the present invention is primarily directed towards the monitoring of human beings, the invention has also been proven to be applicable for monitoring animals, in particular mammals. Consequently, the term "patient" should be interpreted as covering both human and animal patients.

The inventive concept is not limited to the exemplary embodiments described above. Rather, the scope of the invention is set forth in the following patent claims.

The invention claimed is:

1. Method for monitoring the state of the autonomous nervous system of a sedated patient, the method being executed by a processing device in an apparatus for monitoring the state of the autonomous nervous system of the sedated patient, the method comprising the steps of:

measuring a skin conductance signal at an area of the patient's skin during a measurement interval using a skin conductance measuring device, inputting the skin conductance signal in the processing device, said processing device being adapted to identify local minimum points in the skin conductance signal through the measurement interval, causing the processing device to identify local minimum points in the skin conductance signal through the measurement interval, causing the processing device to select intervals between said identified, subsequent minimum points as integrating intervals, for each integrating interval,
  causing the processing device to calculate a linear ramp function defined by the skin conductance signal at the starting point and the ending point of the integrating interval,
  in subsets of the integrating interval wherein the skin conductance signal exceeds the linear ramp function, calculating the integral of the difference between the skin conductance signal and the linear ramp function, and causing the processing device to calculate the sum of said integrals through the measurement interval as a first measure, whereby the result provided by the processing device reflects the state of the autonomous nervous system of said sedated patient.

2. Method according to claim 1, the method further comprising the steps of selecting a subset of the measurement interval, starting at the first minimum point in the measurement interval, selecting the skin conductance value at the first minimum point in the measurement interval as a constant value, in subsets of the measurement interval subset wherein the skin conductance signal exceeds the constant value, calculating the integral of the difference between the skin conductance signal and the constant value, and calculating a sum of the integrals that were calculated in each of the subsets of the measurement interval as a second measure that reflects the state of the autonomous nervous system of said sedated patient.

3. Method according to claim 2, wherein the endpoint of said subset of the measurement interval is selected at the last minimum point of the skin conductance value through the measurement interval.

4. Method according to claim 2, wherein the endpoint of said subset of the measurement interval is selected at the last point in the measurement interval.

5. Method according to claim 2, further comprising the step of providing the largest of the first and second measures as an output signal that reflects the state of the autonomous nervous system of the sedated patient.

6. Method according to claim 5, further comprising the step of displaying said output signal on a display.

7. Method according to claim 6, wherein said measurement interval is in the range 5 to 30 seconds.

8. Method according to claim 7, further comprising the step of setting a pain indication signal if the output signal is within a predetermined range of output signal values, the predetermined range having a lower limit value and a higher limit value.

9. Method according to claim 8, wherein the lower limit value is in the range <0.05 µSs, 0.20 µSs>, and wherein the higher limit value is in the range <0.5 µSs, 3.0 µSs>.

10. Method according to claim 9, further comprising the step of setting an awakening indication signal if the output signal is larger than a predetermined output signal value.

11. Method according to claim 10, wherein the predetermined output signal value is in the range <0.5 µSs, 3.0 µSs>.

12. Method according to claim 1, further comprising the preceding step of exerting a pain inducing stimulus such as a standardised noxious stimulus to the patient.

* * * * *